(12) United States Patent
Braithwaite

(10) Patent No.: US 8,800,550 B2
(45) Date of Patent: *Aug. 12, 2014

(54) MEDICAMENT DELIVERY ASSEMBLY

(75) Inventor: Philip Braithwaite, Tewkesbury (GB)

(73) Assignee: Innovata Biomed Limited, Edinburgh (GB)

( * ) Notice: Subject to any disclaimer, the term of this patent is extended or adjusted under 35 U.S.C. 154(b) by 772 days.

This patent is subject to a terminal disclaimer.

(21) Appl. No.: 12/324,330

(22) Filed: Nov. 26, 2008

(65) Prior Publication Data

US 2009/0145432 A1 Jun. 11, 2009

Related U.S. Application Data

(63) Continuation of application No. 10/496,169, filed as application No. PCT/GB02/05272 on Nov. 22, 2002, now Pat. No. 7,464,704.

(30) Foreign Application Priority Data

Nov. 23, 2001 (GB) .................................. 0128148.4

(51) Int. Cl.
*A61M 11/00* (2006.01)

(52) U.S. Cl.
USPC ................................ 128/200.21; 128/200.12

(58) Field of Classification Search
USPC ............ 128/200.21, 200.22, 203.12, 203.15, 128/203.21, 200.12
See application file for complete search history.

(56) References Cited

U.S. PATENT DOCUMENTS

| | | | |
|---|---|---|---|
| 1,858,735 A | | 5/1932 | Goodsell |
| 2,587,215 A | | 2/1952 | Priestly |
| 2,844,361 A | * | 7/1958 | Dilcher et al. ................. 366/106 |
| 2,919,159 A | * | 12/1959 | Lacroix .......................... 406/137 |
| 3,008,609 A | | 11/1961 | Sessions |
| 3,162,332 A | * | 12/1964 | Hayim ........................... 222/630 |
| 3,439,823 A | | 4/1969 | Morane |
| 3,798,054 A | | 3/1974 | Kawata et al. |
| 3,854,626 A | | 12/1974 | Krechmar |
| 3,856,185 A | | 12/1974 | Riccio |
| 3,874,381 A | | 4/1975 | Baum |

(Continued)

FOREIGN PATENT DOCUMENTS

| | | |
|---|---|---|
| CA | 2395588 A1 | 6/2001 |
| DE | 14 98 398 | 1/1969 |

(Continued)

OTHER PUBLICATIONS

Gerrity, "Pathophysiological and Disease Constraints on Aerosol Delivery," Chapter 1, *Respiratory Drug Delivery I*, ed. Byron, P.R., CRC Press, pp. 1 38 (1990).

(Continued)

*Primary Examiner* — Steven Douglas
(74) *Attorney, Agent, or Firm* — LeClairRyan, a Professional Corporation

(57) ABSTRACT

The disclosure relates to a medicament delivery assembly that has a mouthpiece provided with an air amplifier and a primer source, where the mouthpiece and the air amplifier are each connected to the primer source via an actuatable valve. The air amplifier is also provided with a medicament extraction tube such that when the actuatable valve is opened, the primer source is activated and causes air to flow to the air amplifier. There is also described a method of administering a medicament using such a medicament delivery assembly.

18 Claims, 17 Drawing Sheets

(56) References Cited

U.S. PATENT DOCUMENTS

| | | | |
|---|---|---|---|
| 3,876,269 A | 4/1975 | Fisher et al. | |
| 4,047,635 A | 9/1977 | Bennett, Jr. | |
| 4,114,615 A | 9/1978 | Wetterlin | |
| 4,118,074 A * | 10/1978 | Solt | 406/85 |
| 4,174,034 A | 11/1979 | Hoo | |
| 4,200,099 A | 4/1980 | Guenzel et al. | |
| 4,274,403 A | 6/1981 | Struve | |
| 4,524,769 A | 6/1985 | Wetterlin | |
| 4,534,343 A | 8/1985 | Nowacki et al. | |
| 4,570,630 A | 2/1986 | Elliott et al. | |
| 4,604,847 A | 8/1986 | Moulding, Jr. et al. | |
| 4,624,442 A | 11/1986 | Duffy et al. | |
| 4,627,432 A | 12/1986 | Newell et al. | |
| 4,635,829 A | 1/1987 | Brittingham, Jr. | |
| 4,668,218 A | 5/1987 | Virtanen | |
| 4,799,831 A * | 1/1989 | Ariaz | 406/136 |
| 4,811,731 A | 3/1989 | Newell et al. | |
| 4,860,740 A | 8/1989 | Kirk et al. | |
| 4,882,210 A | 11/1989 | Romberg et al. | |
| 4,895,719 A | 1/1990 | Radhakrishnan et al. | |
| 4,907,583 A | 3/1990 | Wetterlin et al. | |
| 4,934,358 A | 6/1990 | Nilsson et al. | |
| 5,002,048 A | 3/1991 | Makiej, Jr. | |
| 5,007,419 A | 4/1991 | Weinstein et al. | |
| 5,042,472 A | 8/1991 | Bunin | |
| 5,053,237 A | 10/1991 | Hendricks et al. | |
| 5,064,083 A | 11/1991 | Alexander et al. | |
| 5,067,491 A | 11/1991 | Taylor, II et al. | |
| 5,071,289 A * | 12/1991 | Spivak | 406/11 |
| 5,113,855 A | 5/1992 | Newhouse | |
| 5,152,422 A | 10/1992 | Springer | |
| 5,154,326 A | 10/1992 | Chang et al. | |
| 5,161,524 A | 11/1992 | Evans | |
| 5,169,029 A | 12/1992 | Behar et al. | |
| 5,192,528 A | 3/1993 | Radhakrishnan et al. | |
| 5,207,217 A | 5/1993 | Cocozza et al. | |
| 5,208,226 A | 5/1993 | Palmer | |
| 5,222,529 A * | 6/1993 | Zoltan et al. | 141/4 |
| 5,253,782 A | 10/1993 | Gates et al. | |
| 5,263,475 A | 11/1993 | Altermatt et al. | |
| 5,295,479 A | 3/1994 | Lankinen | |
| 5,301,666 A | 4/1994 | Lerk et al. | |
| 5,347,999 A | 9/1994 | Poss et al. | |
| 5,351,683 A | 10/1994 | Chiesi et al. | |
| 5,388,572 A * | 2/1995 | Mulhauser et al. | 128/203.15 |
| 5,394,868 A | 3/1995 | Ambrosio et al. | |
| 5,409,132 A | 4/1995 | Kooijmans et al. | |
| 5,411,175 A | 5/1995 | Armstrong et al. | |
| 5,415,162 A | 5/1995 | Casper et al. | |
| 5,435,301 A | 7/1995 | Herold et al. | |
| 5,437,267 A | 8/1995 | Weinstein et al. | |
| 5,437,270 A | 8/1995 | Braithwaite | |
| 5,447,151 A | 9/1995 | Bruna et al. | |
| 5,450,160 A | 9/1995 | Tianello et al. | |
| 5,458,135 A | 10/1995 | Patton et al. | |
| 5,485,939 A | 1/1996 | Tucker | |
| 5,503,144 A | 4/1996 | Bacon | |
| 5,520,166 A | 5/1996 | Ritson et al. | |
| 5,524,613 A | 6/1996 | Haber et al. | |
| 5,551,597 A | 9/1996 | Lambelet, Jr. et al. | |
| 5,562,231 A | 10/1996 | Lambelet, Jr. et al. | |
| 5,562,918 A | 10/1996 | Stimpson | |
| 5,570,686 A * | 11/1996 | Century | 128/203.12 |
| 5,575,280 A | 11/1996 | Gupte et al. | |
| 5,617,845 A | 4/1997 | Poss et al. | |
| 5,622,166 A | 4/1997 | Eisele et al. | |
| 5,653,227 A | 8/1997 | Barnes et al. | |
| 5,657,748 A | 8/1997 | Braithwaite | |
| 5,657,794 A | 8/1997 | Briner et al. | |
| 5,664,557 A | 9/1997 | Makicj, Jr. | |
| 5,664,697 A | 9/1997 | Lambelet, Jr. et al. | |
| 5,676,130 A | 10/1997 | Gupte et al. | |
| 5,678,538 A | 10/1997 | Drought | |
| D389,570 S | 1/1998 | Savolainen | |
| 5,740,792 A | 4/1998 | Ashley et al. | |
| 5,740,794 A | 4/1998 | Smith et al. | |
| 5,775,536 A | 7/1998 | Lambelet, Jr. et al. | |
| 5,778,873 A | 7/1998 | Braithwaite | |
| 5,785,049 A | 7/1998 | Smith et al. | |
| 5,799,821 A | 9/1998 | Lambelet, Jr. et al. | |
| 5,826,570 A * | 10/1998 | Goodman et al. | 128/200.14 |
| 5,857,457 A | 1/1999 | Hyppölä | |
| 5,875,776 A | 3/1999 | Vaghefi | |
| 5,881,719 A | 3/1999 | Gottenauer et al. | |
| 5,896,855 A | 4/1999 | Hobbs et al. | |
| 5,904,139 A | 5/1999 | Hauser | |
| 5,921,237 A | 7/1999 | Eisele et al. | |
| 5,924,417 A | 7/1999 | Braithwaite | |
| 5,941,241 A | 8/1999 | Weinstein et al. | |
| 5,944,660 A | 8/1999 | Kimball et al. | |
| 5,955,439 A | 9/1999 | Green | |
| 5,981,549 A | 11/1999 | Viner | |
| 5,996,577 A | 12/1999 | Ohki et al. | |
| 6,006,747 A | 12/1999 | Eisele et al. | |
| 6,035,463 A | 3/2000 | Pawelzik et al. | |
| 6,065,471 A | 5/2000 | Schaeffer et al. | |
| 6,065,472 A | 5/2000 | Anderson et al. | |
| 6,076,521 A | 6/2000 | Lindahl et al. | |
| 6,089,227 A | 7/2000 | Nilsson | |
| 6,116,238 A | 9/2000 | Jackson et al. | |
| 6,116,239 A | 9/2000 | Volgyesi | |
| 6,119,688 A | 9/2000 | Whaley et al. | |
| 6,125,844 A | 10/2000 | Samiotes | |
| 6,138,668 A * | 10/2000 | Patton et al. | 128/200.14 |
| 6,158,675 A | 12/2000 | Ogi | |
| 6,196,218 B1 | 3/2001 | Voges | |
| 6,220,243 B1 | 4/2001 | Schaeffer et al. | |
| 6,234,167 B1 | 5/2001 | Cox et al. | |
| 6,240,918 B1 | 6/2001 | Ambrosio et al. | |
| 6,254,854 B1 | 7/2001 | Edwards et al. | |
| 6,273,085 B1 | 8/2001 | Eisele et al. | |
| 6,321,747 B1 | 11/2001 | Dmitrovic et al. | |
| 6,324,428 B1 | 11/2001 | Weinberg et al. | |
| 6,325,241 B1 | 12/2001 | Garde et al. | |
| 6,328,034 B1 | 12/2001 | Eisele et al. | |
| 6,347,629 B1 | 2/2002 | Braithwaite | |
| 6,418,926 B1 | 7/2002 | Chawla | |
| 6,443,146 B1 | 9/2002 | Voges | |
| 6,484,718 B1 | 11/2002 | Schaeffer et al. | |
| 6,523,536 B2 | 2/2003 | Fugelsang et al. | |
| 6,543,443 B1 | 4/2003 | Klimowicz et al. | |
| 6,553,987 B1 | 4/2003 | Davies | |
| 6,557,550 B1 | 5/2003 | Clarke | |
| 6,557,552 B1 | 5/2003 | Cox et al. | |
| 6,601,729 B1 | 8/2003 | Papp | |
| 6,616,914 B2 | 9/2003 | Ward et al. | |
| 6,675,839 B1 | 1/2004 | Braithwaite | |
| 6,679,256 B2 | 1/2004 | Ingle et al. | |
| 6,681,767 B1 * | 1/2004 | Patton et al. | 128/203.15 |
| 6,698,425 B1 | 3/2004 | Widerström | |
| 6,779,520 B2 * | 8/2004 | Genova et al. | 128/200.22 |
| 6,810,873 B1 | 11/2004 | Haikarainen et al. | |
| 6,810,874 B1 | 11/2004 | Koskela et al. | |
| 6,845,772 B2 * | 1/2005 | Braithwaite et al. | 128/203.15 |
| 6,926,003 B2 | 8/2005 | Seppälä | |
| 7,464,704 B2 | 12/2008 | Braithwaite | |
| 2003/0075172 A1 | 4/2003 | Johnson et al. | |
| 2003/0116157 A1 | 6/2003 | Braithwaite et al. | |
| 2003/0136406 A1 | 7/2003 | Seppala | |
| 2004/0011357 A1 | 1/2004 | Braithwaite | |
| 2004/0101482 A1 | 5/2004 | Sanders | |
| 2004/0236282 A1 | 11/2004 | Braithwaite | |
| 2004/0251318 A1 | 12/2004 | Braithwaite | |
| 2007/0272763 A1 * | 11/2007 | Dunne et al. | 239/8 |

FOREIGN PATENT DOCUMENTS

| | | |
|---|---|---|
| DE | 23 46 730 A | 4/1975 |
| DE | 32 43 731 A | 5/1984 |
| DE | 195 30 240 | 2/1997 |
| DE | 197 57 207 A1 | 6/1999 |
| EP | 0 045 522 A2 | 2/1982 |
| EP | 0 079 478 A1 | 5/1983 |
| EP | 0 166 294 B1 | 10/1989 |

(56) References Cited

FOREIGN PATENT DOCUMENTS

| | | |
|---|---|---|
| EP | 0 469 814 A1 | 2/1992 |
| EP | 0 514 085 B1 | 11/1992 |
| EP | 0 520 440 A1 | 12/1992 |
| EP | 0 372 777 B1 | 1/1993 |
| EP | 0 548 605 B1 | 6/1993 |
| EP | 0 424 790 B1 | 8/1993 |
| EP | 0 573 128 A | 12/1993 |
| EP | 0 626 689 B1 | 11/1994 |
| EP | 0 448 204 B1 | 4/1995 |
| EP | 0 539 469 B1 | 4/1995 |
| EP | 0 659 432 A1 | 6/1995 |
| EP | 0 663 815 B1 | 7/1995 |
| EP | 1 062 962 A | 12/2000 |
| EP | 1 106 196 A | 6/2001 |
| EP | 1 208 863 A | 5/2002 |
| FR | 2 516 387 A | 5/1983 |
| FR | 2 584 604 A | 1/1987 |
| FR | 2 662 936 A | 12/1991 |
| FR | 2 753 791 | 3/1998 |
| GB | 3908 | 0/1911 |
| GB | 1 242 211 | 8/1971 |
| GB | 1 573 551 | 8/1980 |
| GB | 2 041 763 A | 9/1980 |
| GB | 2 165 159 A | 4/1986 |
| GB | 2 178 965 A | 2/1987 |
| GB | 2 235 753 A | 3/1991 |
| GB | 2 248 400 A | 4/1992 |
| GB | 2 366 208 A | 3/2002 |
| JP | H8-103499 A | 4/1996 |
| WO | WO 90/07351 | 7/1990 |
| WO | WO 91/04011 | 4/1991 |
| WO | WO 91/11173 | 8/1991 |
| WO | WO 91/11495 | 8/1991 |
| WO | WO 91/14422 | 10/1991 |
| WO | WO 92/00771 | 1/1992 |
| WO | WO 92/03175 | 3/1992 |
| WO | WO 92/04928 | 4/1992 |
| WO | WO 92/09322 | 6/1992 |
| WO | WO 92/18188 | 10/1992 |
| WO | WO 93/00951 | 1/1993 |
| WO | WO 93/11746 | 6/1993 |
| WO | WO 93/16748 | 9/1993 |
| WO | WO 95/00128 | 1/1995 |
| WO | WO 95/15777 | 6/1995 |
| WO | WO 97/00399 | 1/1997 |
| WO | WO 98/26828 | 6/1998 |
| WO | WO 98/30262 | 7/1998 |
| WO | WO 98/31352 | 7/1998 |
| WO | WO 99/12597 | 3/1999 |
| WO | WO 99/13930 | 3/1999 |
| WO | WO 99/26676 | 6/1999 |
| WO | WO 00/01434 A1 | 1/2000 |
| WO | WO 00/12163 | 3/2000 |
| WO | WO 00/45878 | 8/2000 |
| WO | WO 00/64519 | 11/2000 |
| WO | WO 01/17595 A1 | 3/2001 |
| WO | WO 01/39823 A | 6/2001 |
| WO | WO 01/51030 A1 | 7/2001 |
| WO | WO 01/60341 A1 | 8/2001 |
| WO | WO 01/87378 A2 | 11/2001 |
| WO | WO 02/056948 A | 7/2002 |
| WO | WO 2004/091705 A | 10/2004 |

OTHER PUBLICATIONS

International Search Report for International Patent Application No. PCT/GB02/05272 (Sep. 18, 2003).

Written Opinion of the International Searching Authority for International Patent Application No. PCT/GB02/05272.

* cited by examiner

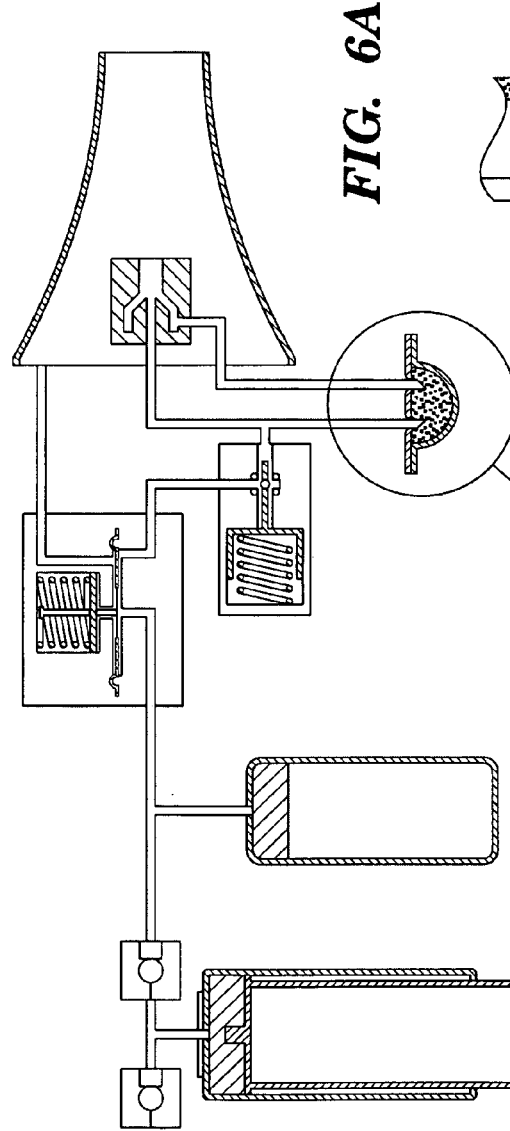
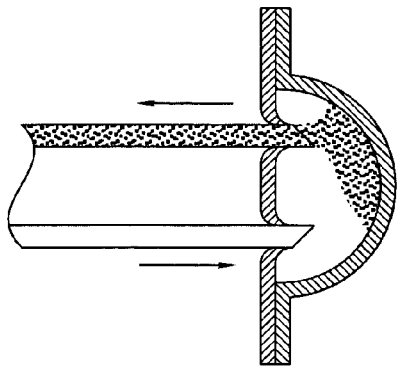
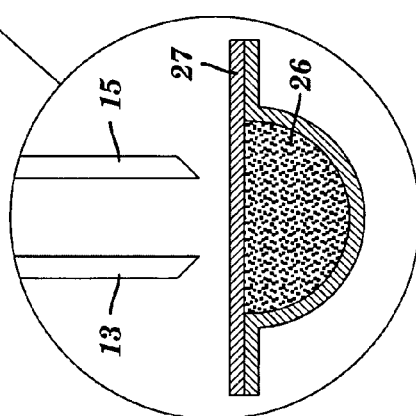

MEDICAMENT DELIVERY ASSEMBLY

This application is a continuation of U.S. patent application Ser. No. 10/496,169, filed Jan. 7, 2005, which is the U.S. national stage of International Patent Application No. PCT/GB02/05272, filed Nov. 22, 2002, which claims the priority benefit of Great Britain Patent Application No. 0128148.4, filed Nov. 23, 2001, each of which is hereby incorporated by reference in its entirety.

This invention relates to a novel medicament delivery assembly, for example, a medicament delivery assembly, such as an inhaler. In particular the invention provides a novel form of dry powder inhaler and a method of delivering a powder using such an inhaler.

Conventional dry powder inhalers (DPIs) deliver a powder dosage by the aerosolisation of the powder caused when a patient inhales. One disadvantage with DPIs is that the extent of aerosolisation, and therefore the consistency of the dosage delivered, is dependent upon, inter alia, the inspiratory flow of the patient, the nature of the air passage and the nature of the formulation.

Attempts have been made to improve on conventional DPIs by using, for example, an air jet directed at or across a powder. However, such systems suffer from a number of disadvantages in that, inter alia, (i) A powder container may be difficult to completely empty, giving rise to problems in dosage consistency. There may also be a lack of any real element of control of the air stream.
(ii) There is no amplification, i.e.; the volume of air entering the assembly is the same as the volume of air leaving the assembly, which may limit the efficiency of powder aerosolisation.
(iii) Air flowing across the powder can only lift the powder into the air stream and therefore does not efficiently aerosolise the powder.

Conventional metered dose inhalers (MDIs) attempt to address this problem by the use of a volatile propellant to create a pressure sufficient to aerosolise the medicament. However, one disadvantage of MDIs is that the combination of a volatile propellant to create a pressure sufficient to aerosolise the medicament and a solubilised medicament can give rise to blocking or clogging of the valve through which the aerosolised medicament is emitted. In addition MDIs are disadvantageous in that they lack the ability to co-ordinate actuation with inhalation, impaction in the oropharynx, etc.

U.S. Pat. No. 6,158,676 to Nathaniel Hughes, describes a microatomising assembly which uses a vortex accumulation resonant chamber which creates a vacuum to enable outside entrainment air to be drawn into the assembly, lowering the speed of delivery of the medicament particles to the lung.

U.S. Pat. No. 5,657,749 describes a dry powder inhaler which is provided with a curved section of a passage which creates a Venturi effect to empty a powder containing depression. However, deagglomeration and/or aerosolisation of the powder is still dependent upon, inter alia, the inspiration rate of the patient. Furthermore, although the assembly addresses the problem of complete emptying of the powder container by the utilisation of a walled passage which communicates and co-operates with a depression in the powder container to create a Venturi effect, such a assembly does not address the problems of prior art MDIs or DPIs.

Thus there has long been a need for a medicament delivery assembly which is capable of overcoming the aforementioned disadvantages.

We have now developed a medicament delivery assembly which may comprise a number of different, controllable, elements and therefore overcomes or mitigates the disadvantages of the prior art. In particular the medicament delivery assembly of the present invention overcomes the problem of MDIs by separation of the volatile propellant fluid and the medicament. Furthermore, the medicament delivery assembly of the invention overcomes or mitigates the problems associated with prior art DPI devices and provides a greater efficiency of aerosolisation and lung delivery.

Thus, according to the invention we provide a medicament delivery assembly which comprises mouthpiece provided with an air amplifier and a primer source, wherein the mouthpiece and the air amplifier are each is connected to the primer source via an actuatable valve; the air amplifier is also provided with a medicament extraction tube such that when the actuatable valve is opened then the primer source is activated and causes air to flow to the air amplifier.

In a preferred embodiment of the invention when the primer source is activated air also flows to the mouthpiece. Preferably, the mouthpiece and the air amplifier are each separately connected to the primer source, i.e. via the actuable valve. Optionally, the air may be caused to flow to the air amplifier via a pulse valve. In particular the assembly of the invention utilises an amplified gas stream to disperse a medicament, e.g. a powder. An unamplified gas steam is created of sufficient velocity, so that, as it passes across a first opening of a contiguous chamber or conduit it creates a vacuum in the chamber or conduit. The chamber or conduit is provided with a medicament reservoir or a medicament metering member and has a second opening, such that an entrained air flow is created through the medicament, from the second to the first opening. This entrained air flow causes amplification of the initial gas stream and acts, inter alia, to aerosolise the medicament. When the medicament is a powder, the entrained airflow may also act to deagglomerate the powder in addition to aerosolising it. For the sake of clarity the terms entrainment, deagglomeration and aerosolisation used herein are intended to have the following meanings:

deagglomeration—to break up into smaller parts
entrainment—being lifted into an air stream
aerosolisation—to be suspended in air or an air stream The assembly of the invention especially utilises an air amplifying system comprising an amplifying fluid jet provided with a fluid inlet and a fluid outlet, the fluid outlet being linked to an outlet nozzle via an amplifying passage, the amplifying passage also being linked to a medicament chamber, said chamber being adapted for non-laminar medicament flow, such that fluid travelling from the fluid outlet of the jet draws extraneous air and aerosolised medicament through the medicament chamber so that the extraneous air and aerosolised medicament mix with the amplifying fluid in the amplifying passage and the amplified mixture exits through the outlet nozzle.

In particular, in the case of a powdered medicament, the assembly of the invention provides a greater efficiency of deagglomeration and/or aerosolisation over prior art devices. Such a vacuum is sometimes referred to as a Venturi effect vacuum. The effect of the vacuum is to deagglomerate the powder without direct impingement of the gas stream on the powder. Moreover, the gas stream can also be adapted to utilise the Coanda effect. The Coanda effect is caused by the deflection of a gas stream against a solid surface, the effect being the tendency of the flow to become attached to or flow around the solid surface. The exploitation of this effect, therefore enables a 'shape' to be given to the existing gas stream.

Our co-pending International Patent application No. PCT/GB02/02251 describes an air amplifying powder delivery device which comprises a delivery passage provided with an outlet, a powder reservoir and a metering member adapted to present a measured dose of powder to the delivery passage, characterised in that the delivery assembly is provided with means for creating an entrained air flow through the medicament, e.g. powder, reservoir and/or metering member sufficient to deagglomerate the powder. The aforementioned International application describes an air amplifying system comprising an amplifying fluid jet provided with a fluid inlet and a fluid outlet, the fluid outlet being linked to an outlet nozzle via an amplifying passage, the amplifying passage also being led to a medicament chamber, said chamber being adapted for non-laminar medicament flow, such that fluid travelling from the fluid outlet of the jet draws extraneous air and aerosolised medicament through the medicament chamber so that the extraneous air and aerosolised medicament mix with the amplifying fluid in the amplifying passage and the amplified mixture exits through the outlet nozzle. Medicament formulations, and especially powdered medicament formulations, generally require handling/manipulating in a delivery assembly in a carefully controlled manner in order that, inter alia, a patient may receive the formulation at the target area of the lung in its required state. That is to say the patient will receive:—the correct amount;

the specified fine particle fraction;

in a stable state; and at the correct point of inspiration.

These essential requirements mean that, inter alia, the medicament has to be:

a) Accurately formulated (manufactured).
b) Correctly metered into unit dose containers.
c) The container must adequately protect the medicament to maintain stability of the formulation.
d) When the medicament is extracted from the unit dose contained, as close to 100% collection is required.
e) The medicament on route from the container to the target area should be conditioned/handled in such a manner that the particle site distribution as determined by the fire particle fraction is consistently in specification and high.
f) The emitted dose should be as close to 100% of the metered dose.
g) The quality of the delivered dose should be independent of the patients inspiratory flow rate.
h) The point of release into the patient's inspiratory flow should be controlled and consistent
i) The rate of release or impact of assembly design should effectively slow aerosol cloud to reduce oropharyngeal deposition.

A number of the requirements mentioned above present challenges on their own but some of them together present significant difficulties, for example, containing a unit dose of medicament in a moisture proof container such that medicament can subsequently be completely cleared and efficiently aerosolised from the assembly.

We have now developed an assembly which may work in conjunction with an air amplifier, such as that described in International Patent application No. PCT/GB02/02251.

The medicament reservoir may comprise any conventionally known reservoir. Thus, the reservoir may comprise a bulk medicament reservoir and therefore be accompanied by one or more metering members. Alternatively, the reservoir may comprise a plurality of individual dosage units, such as, capsules, blisters, spools, etc. In a preferred embodiment, the reservoir comprises a pre-filled metering members, e.g. in the form of blister or strip of blisters.

The air amplifier used in the assembly of the invention preferentially comprises a device, such as is described in our co-pending International application No. PCT/GB02/02251 which is incorporated herein by reference.

Thus, preferentially the air amplifier comprises means for creating an entrained flow through the medicament reservoir and/or metering member comprises an air inlet, preferentially adjacent to the medicament reservoir and/or metering member, and means for creating a pressure differential sufficient to draw-entrained air through the inlet. It should be understood that the basis of the present invention is the creation of a pressure differential which, in the case of a powdered medicament, enables deagglomeration of the medicament. Therefore, the creation of a pressure differential will generally comprise the creation of a vacuum. It is especially preferred that the entrained air will flow through the powder which is presented either direct from the reservoir or, preferentially from the metering member. Thus, preferably, the entrained air inlet will be positioned adjacent to a first side of the reservoir and/or metering member and the vacuum is created adjacent to a second, opposite side of the reservoir and/or metering member.

It is further preferred that the entrained air flow is sufficient to both deagglomerate and aerosolise the powder.

The means for creating a pressure differential may, preferentially, comprise a fluid inlet, a fluid transit chamber and a fluid outlet. In a preferred embodiment the fluid outlet and the outlet of the delivery passage are coincident. The size and shape of the fluid outlet and/or the delivery passage outlet may vary depending upon inter alia, the nature of the medicament, the magnitude of the pressure used, etc.

In one embodiment of the invention the fluid transit chamber may substantially form the body of the delivery assembly and the medicament delivery passage is axial to the body. The medicament reservoir and/or metering member may be contiguous with the fluid transit chamber or may be connected to the pressure differential means by one or more conduits. In this particular embodiment the fluid transit chamber may be a thin annular chamber. The thin annular chamber may be created by bringing together male and female portions. Therefore, the outlet end of the delivery passage may comprise, or alternatively, may be fitted to, a frusto conical male member which fits into an outer portion of the transit chamber in the form of a female member. Preferably, the separation between the male and female members is less than the diameter of the fluid inlet and outlet. Thus the fluid flowing from the fluid inlet into the fluid chamber is constricted, increasing its velocity and providing an improved pressure differential. Such an arrangement is often referred to as a Venturi-type system.

However, in a preferred embodiment of the invention the fluid transit chamber is substantially axial to the body of the delivery assembly and the medicament delivery passage comprises an annular chamber which substantially surrounds the fluid transit chamber. Similarly, the annular chamber may be created by bringing together male and female portions. Therefore, the outlet end of the fluid transit chamber may comprise, or alternatively, may be fitted to, a frusto conical male member which fits into an outer portion of the medicament delivery chamber in the form of a female member. This particular embodiment is found to be advantageous in that, inter alia, the fluid flow may have improved velocity and thereby create a greater pressure differential.

In a preferred embodiment of the invention the fluid inlet and the fluid outlet may be coaxial.

In an especially preferred embodiment the fluid flow chamber may be provided with a plurality of outlets, e.g. in the form of jet tubes. Such a plurality of jet tubes may increase the volume of medicament emitted through the delivery passage outlet whilst reducing the total velocity of the fluid. This is especially advantageous in the case of delivery of a powdered medicament, e.g. in an inhaler, since it enables a low velocity aerosolised powder cloud to be generated. In such a case the fluid flow chamber may comprise a plurality of sub-chambers. In which case each sub-chamber may optionally be provided with one or more medicament inlet orifices. Furthermore, the assembly may be arranged to provide the separate, sequential or simultaneous operation of the jets to enable the creation of an aerosolised medicament which coincides with, for example, the inspiration of a patient.

When the vacuum means comprises a Venturi-type system as hereinbefore described the pressurised fluid may be any fluid moving system. The fluid may be a liquid, however, preferentially, the fluid is a gas, for example, compressed air or a gas/vapour generated from the volatilisation of a volatile propellant, such as that delivered from a pressurised canister. Alternatively, the fluid flow may be generated by an electric motor, e.g. a battery operated motor, or by a manually primed piston, e.g. a hand pump.

The primer source may comprise any conventionally known source. Preferably the source will comprise a compressed gas propellant. Thus, for example, the primer may comprise a compressed gas filled canister or other volatile medium.

The propellant filled canister may be connected to an expansion reservoir. Thus, in use, the propellant filled canister may be activated, e.g. by a switch or lever, to release the propellant, or a priming dose of the propellant into a priming or expansion chamber.

When the vacuum means comprises the use of a volatilised propellant, any conventionally known pharmaceutically and/or environmentally acceptable propellants may be utilised. Such propellants include, but are not limited to, non-CFC propellants, such as a hydrofluoroalkane (HFA). Any conventionally known HFA propellant may be used, including those disclosed in, for example, EP0372777, WO91/04011, WO91/11173, WO91/11495 and WO91/14422. However, the most preferred HFA is a fluoroalkane such as a fluoromethane or a fluoroethane or a mixture of fluoroalkanes. Such fluoroalkanes include, but are not limited to, trichlorofluoromethane, dichlorodifluoromethane, 1,2-dichlorotetrafluorethane, trichlorotrifluoroethane and chloropentafluoroethane. One HFA which may be mentioned is HFA 134 (1,1,1,2-tetrafluoroethane) or HFA 227.

The assembly of the invention may, preferably use a diaphragm valve. Preferably the valve is a breath actuated valve, such that it is responsive to the vacuum created by the patients inspiratory flow to initiate the cycle it will be appreciated that there are numerous ways that can be employed to construct a valve or trigger mechanism responsive to the inhalation/exhalation or both of a patient and the invention is not limited to the arrangement described above. Briefly, alternative approaches could include, but are not limited to, mechanical, magnetic, electrical/electronic and memory material devices.

When the valve is a breath actuated valve, any conventionally known breath actuated valve may be used.

It will be appreciated that introducing a device in the passage of the compressed gas to interrupt the flow can be achieved in a variety of ways, including but not limited to electrical, electronic and mechanical.

The use of a container for holding a metered amount of drug formulation has already been described. However, it will be appreciated that the container can be constructed in a variety of ways.

In a further embodiment of the invention, the assembly may also incorporate a pulse valve. Although such a pulse valve is not an essential element of the invention, we have surprisingly found that the use of such a valve provides a very significant increase (more than two-fold) in deposition of the medicament in the lung and also increases clearance of the dose storage unit/medicament reservoir. Thus, the use of a pulse valve in the assembly of the invention is advantageous.

However, we have found that the introduction of a pulse valve is advantageous even if used in conventionally known inhalers. Furthermore, the use of a pulse valve in an inhaler is novel per se.

Thus according to a further aspect of the invention we provide a medicament inhaler which incorporates a pulse valve.

Such a medicament inhaler may be an inhaler known per se. Thus, the inhaler may be a conventionally known metered dose inhaler (MDI) or a conventionally known dry powder inhaler (DPI).

According to this particular aspect of the invention we provide a method of treatment suffering from a disorder treatable by an inhaled medicament which comprises administering the medicament with an inhaler, wherein the inhaler incorporates a pulse valve.

The cycle of the pulse valve may vary depending upon, inter alia, the nature and severity of the disorder being treated, the medicament, etc.

Thus the cycle of the pulse valve may be from 10 to 100 cycles/second, e.g. from 25 to 75 cycles/second.

According to a yet further aspect of the invention we provide a delivery assembly as hereinbefore described characterised in that the assembly is provided with a pulse valve.

The medicament delivery assembly of the invention may be used in conjunction with a variety of delivery devices. However, the medicament delivery assembly is especially suited for use in the delivery of a powdered medicament. The medicament delivery device of the invention has utility in a variety of medicament delivery areas, including, for example, as an inhaler and especially a dry powder inhaler. Such an assembly may be used for the delivery of any type of medicament but the assembly finds particular utility in the delivery of an inhaled powdered medicament. Thus the assembly of the invention may be used as or in conjunction with an inhaler, e.g. a dry powder inhaler.

When the delivery assembly of the invention is utilised as or in conjunction with an inhaler, it is especially advantageous utilisation of entrained air not only deagglomerates the powder but also helps to facilitate aerosolisation of the powder.

Thus according to a fiber feature of the invention we provide a dry powder inhaler characterised in that it incorporates a powder delivery assembly as hereinbefore described.

When the medicament delivery assembly comprises an inhaler, it may comprise a conventionally known inhaler with an assembly of the invention attached thereto. An example of a conventional inhaler is a CLICKHALER (available from Innovata Biomed in the UK and described in European Patent application No. 0 539 469) which is provided with an inhalation passage. The delivery assembly of the invention may optionally be attached, for example, at the outlet end of such an inhaler, to a spacer device.

In one embodiment, the metering member is adapted to transfer measured doses of medicament from the medicament reservoir to the delivery passage.

However, in an alternative embodiment the medicament may be presented to the delivery passage in a closed form, wherein it is opened in the delivery passage. Thus, the metering member may be a capsule, in which case the device may optionally be provided with means for piercing or rupturing the capsule.

In a yet further and preferred embodiment the medicament may be presented to the delivery passage in an open form. Thus, for example, the metering member may be a spool carrying a medicament, in which case the device may be provided with means for presenting the spool in an open form into the delivery member.

Thus, the metering member may comprise a spool housed in a spool carrier. Such spools are generally described in the prior art. An example of such an inhaler assembly is a TECHNOHALER (available from Innovata Biomed in the UK and described in European Patent Application No. 0 626 689). Each spool has a flange at each end which form a tight slidable fit within the body of the spool carrier. The space left between the body of the spool and the spool carrier is filled with an appropriate medicament. In an alternative embodiment the delivery assembly may be provided with a spool chamber, for example, in the form tube adjacent the delivery passage. In a preferred embodiment the spool chamber may form a snug fit around the spool and may therefore replace the spool carrier. The spool chamber may therefore optionally be fitted with an actuator member which may comprise a push rod mechanism.

The delivery assembly of the invention is advantageous in that, inter alia, it may operate by the administration of a dose of aerosolised medicament. The assembly provides a medicament, e.g. a dry powder, delivery system which is independent of the rate of inspiration of a patient, and without the need for a patient to inhale undesirable propellants.

A variety of medicaments may be administered by using the inhaler of the invention. Such medicaments are generally antibiotics, bronchodilators or other anti-asthma drugs. Such medicaments include, but are not limited to $\beta_2$-agonists, e.g. fenoterol, formoterol, pirbuterol, reproterol, rimiterol, salbutamol, salmeterol and terbutaline; non-selective beta-stimulants such as isoprenaline; xanthine bronchodilators, e.g. theophylline, aminophylline and choline theophyllinate; anticholinergics, e.g. ipratropium bromide; mast cell stabilisers, e.g. sodium cromoglycate and ketotifen; bronchial anti-inflammatory agents, e.g. nedocromil sodium; and steroids, e.g. beclomethasone dipropionate, fluticasone, budesonide and flunisolide; and combinations thereof.

It is within the scope of is invention for % to or more medicaments to be administered.

Specific combinations of medicaments which may be mentioned include combinations of steroids, such as, beclomethasone dipropionate, fluticasone, budesonide and flunisolide; and combinations of to $\beta_2$-agonists, such as, formoterol and salmeterol. It is also within the scope of this invention to include combinations of one or more of the aforementioned steroids with one or more of the aforementioned $\beta_2$-agonists.

Further medicaments which may be mentioned include systemically active materials, such as, proteinaceous compounds and/or macromolecules, for example, hormones and mediators, such as insulin, human growth hormone, leuprolide and alpha interferon; growth factors, anticoagulants, immunomodulators, cytokines and nucleic acids.

It is within the scope of his invention to include combinations of any of the aforementioned medicaments.

The particle size of the powder may be varied depending, inter alia, on the type of aerosol being formed. In the case of a dry powder medicament, the particle size of the powder, and the carrier, if one is present. may be varied. The nature of the carrier may also be varied. Thus, the particle size of the powder may be substantially between 1 and 100 μm. That is, at least 90% w/w of the powder should have a particle size of between 1 and 100 μm. The preferred particle size may also depend upon the nature of the powder being delivered. Thus, for example, for the treatment of respiratory disorders a particle size of 4 to 8 μm may be preferred, e.g. 6 μm. However, for the delivery of systematically active powders a smaller particle size may be desirable, for example from 1 to 5 μm, e.g. 3 μm.

In a dry powder formulation a variety of carriers may be used. Certain carriers may be mentioned, by way of example only, such as sugars, e.g. dextran, mannitol and lactose, for example α-lactose monohydrate. The particle size of the carrier may be across a wide range, between 0.1 and 500 μm, preferably between 1 and 200 μm. Alternatively, the carrier may itself comprise a mixture of fine and coarse particles.

According to a flier feature of the invention we provide a method of administering a medicament which comprises the use of a medicament delivery assembly as hereinbefore described.

As previously mentioned the medicament delivery assembly of the invention is especially suited for use as a medicament delivery assembly, e.g. an inhaler. Therefore, we further provide a method of treatment of a patient with a respiratory disorder which comprises the administration of a medicament, e.g. a powdered medicament using an assembly as hereinbefore described. In an especially preferred embodiment the method comprises administration of medicament by inhalation.

In a preferred embodiment we provide a method of treatment of a patient with a systemic disorder which comprises the administration of a medicament using an inhaler as hereinbefore described.

The assembly of the invention is especially suited for the efficient delivery of macromolecules, such as insulin. Thus, according to a particular feature of the invention we provide a method of treating insulin dependent diabetes which comprises administration of an effective amount of insulin using an assembly as hereinbefore described.

When the assembly of the invention is used for the delivery of macromolecules, such as insulin, it is important that they be provided in a moisture resistant system. Thus, according to the invention we provide an assembly as hereinbefore described provided with a moisture resistant coating e.g. a paraxylylene coating.

The invention will now be described by way of example only and with reference to the accompanying drawings in which:

FIG. 1 is a schematic representation of an assembly of the invention;

FIGS. 2A-C are a schematic representation of an assembly of the invention showing the compressed gas source;

FIGS. 3A-C are a schematic representation of an assembly of the invention showing a piston assembly;

Figure 3A:
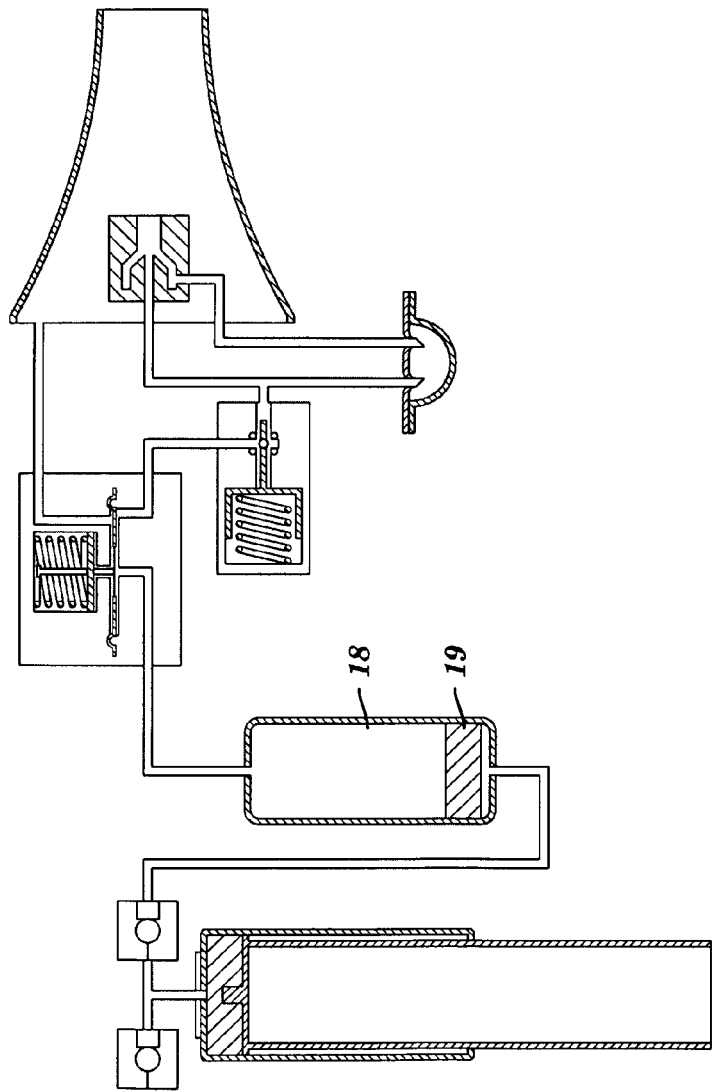
Figure 3B:
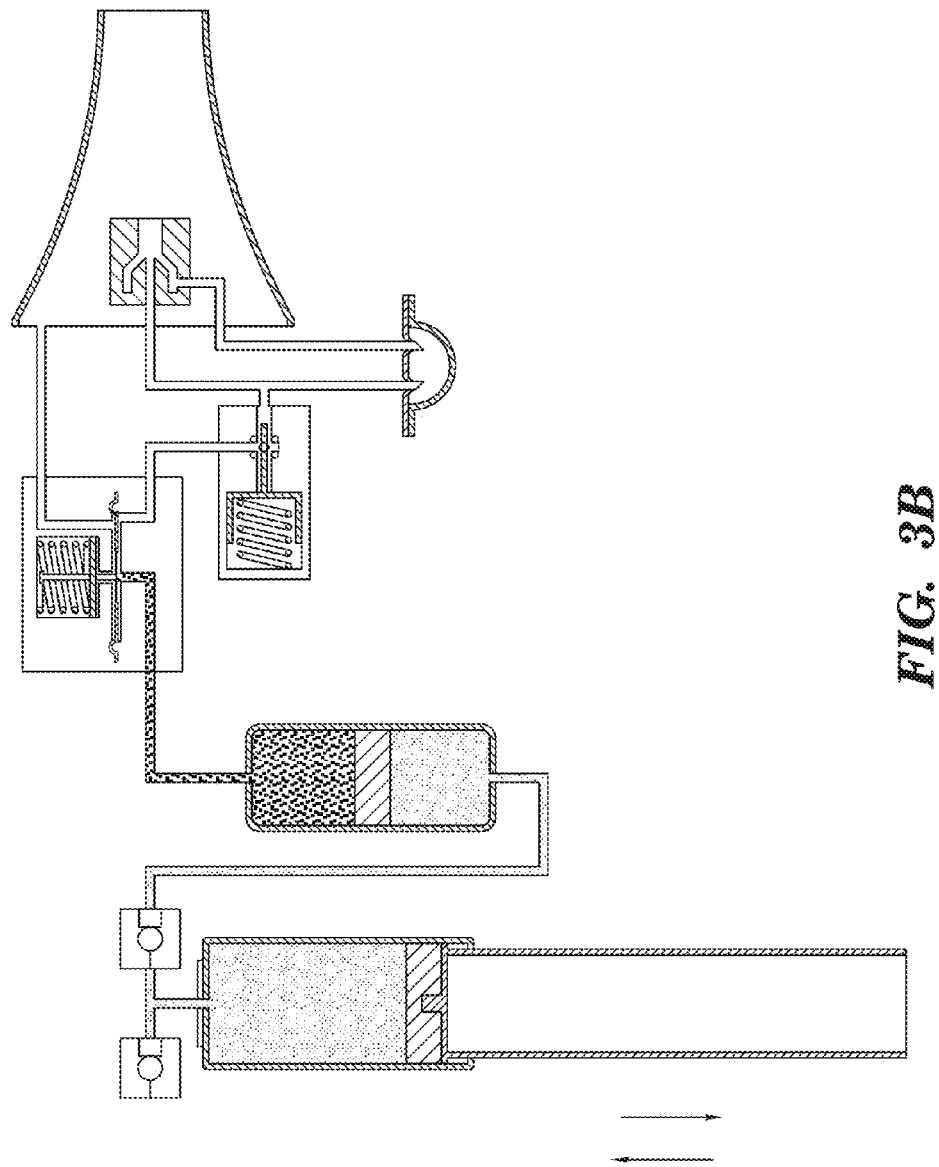
Figure 3C:
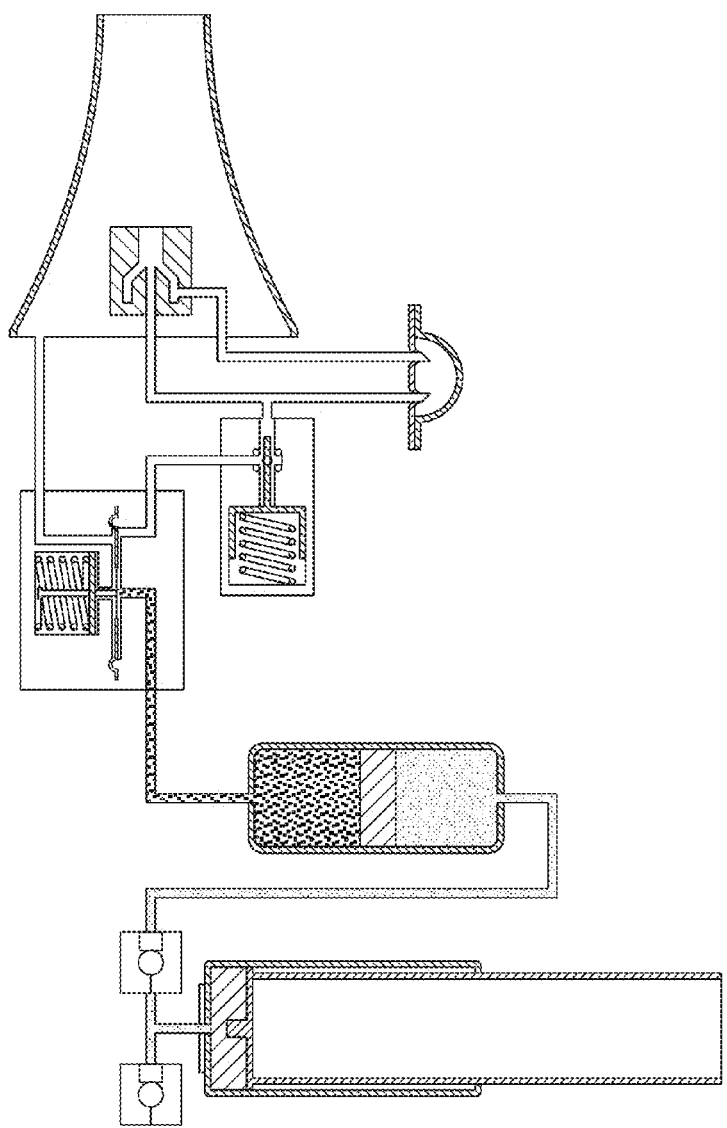
Figure 4:
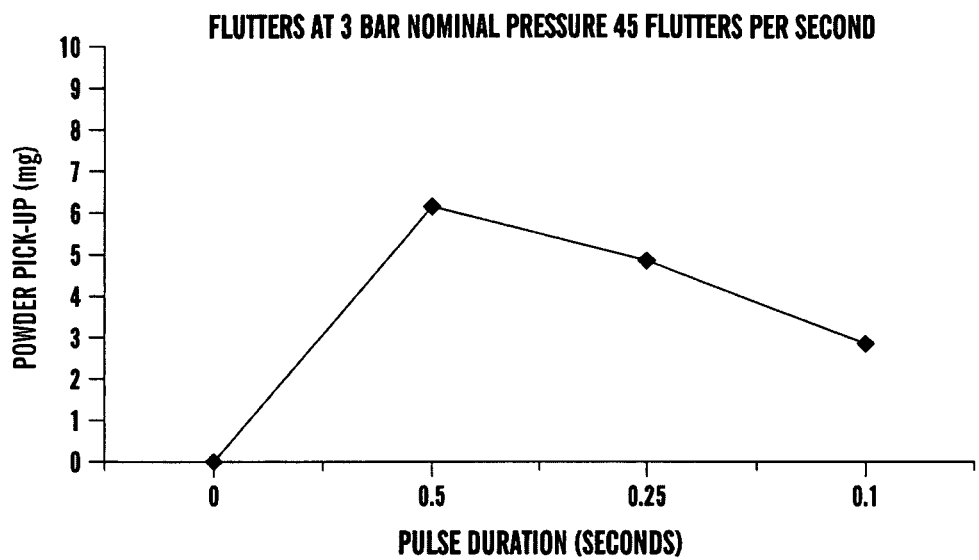
FIG. 4 is a graph illustrating pulse duration at 3 bar; and 45 per second.
Figure 5:
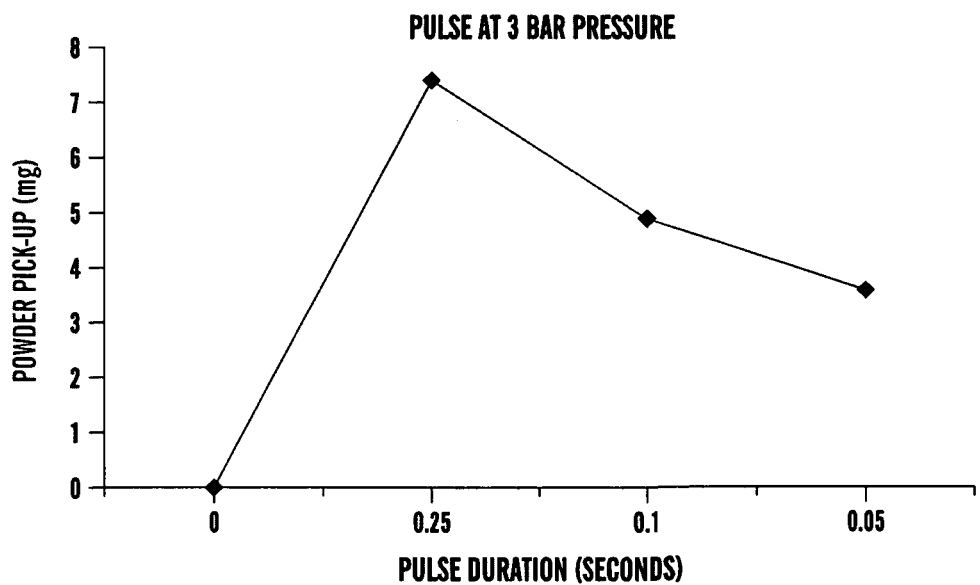
FIG. 5 is a graph showing pulse duration at 3 bar; assembly of the invention.
Figure 7A:
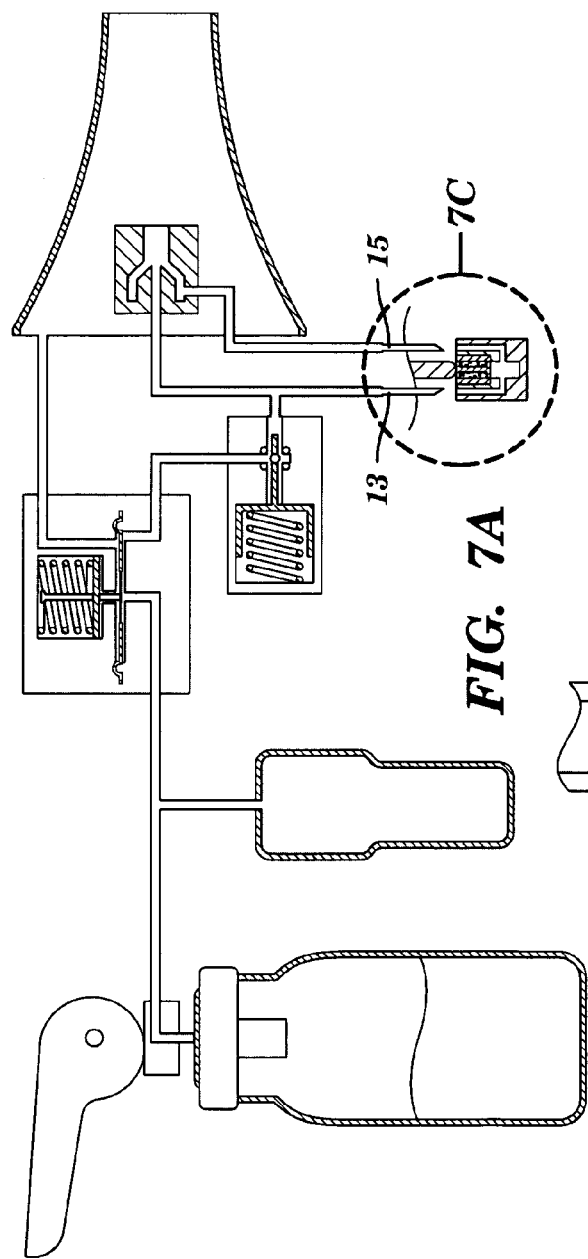
Figure 7B:
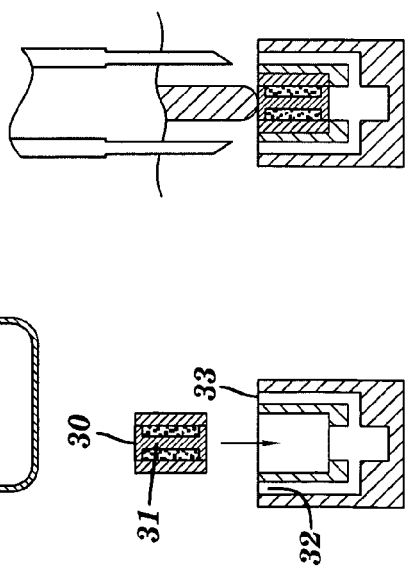
Figure 7C:
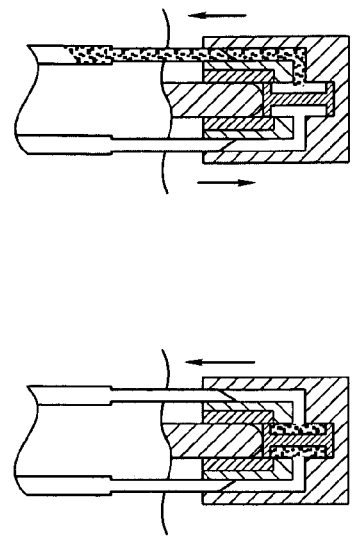
Figure 7D:
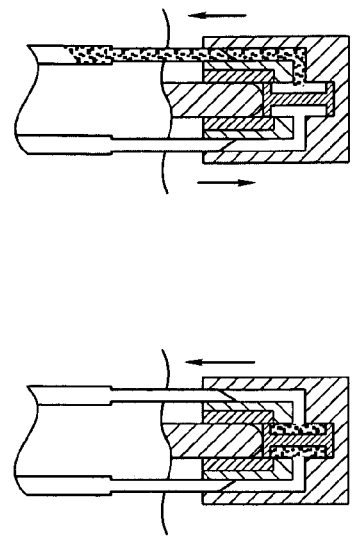
Figure 7E:
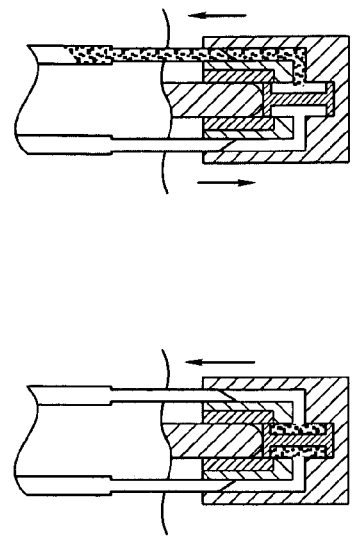
Figure 8A:
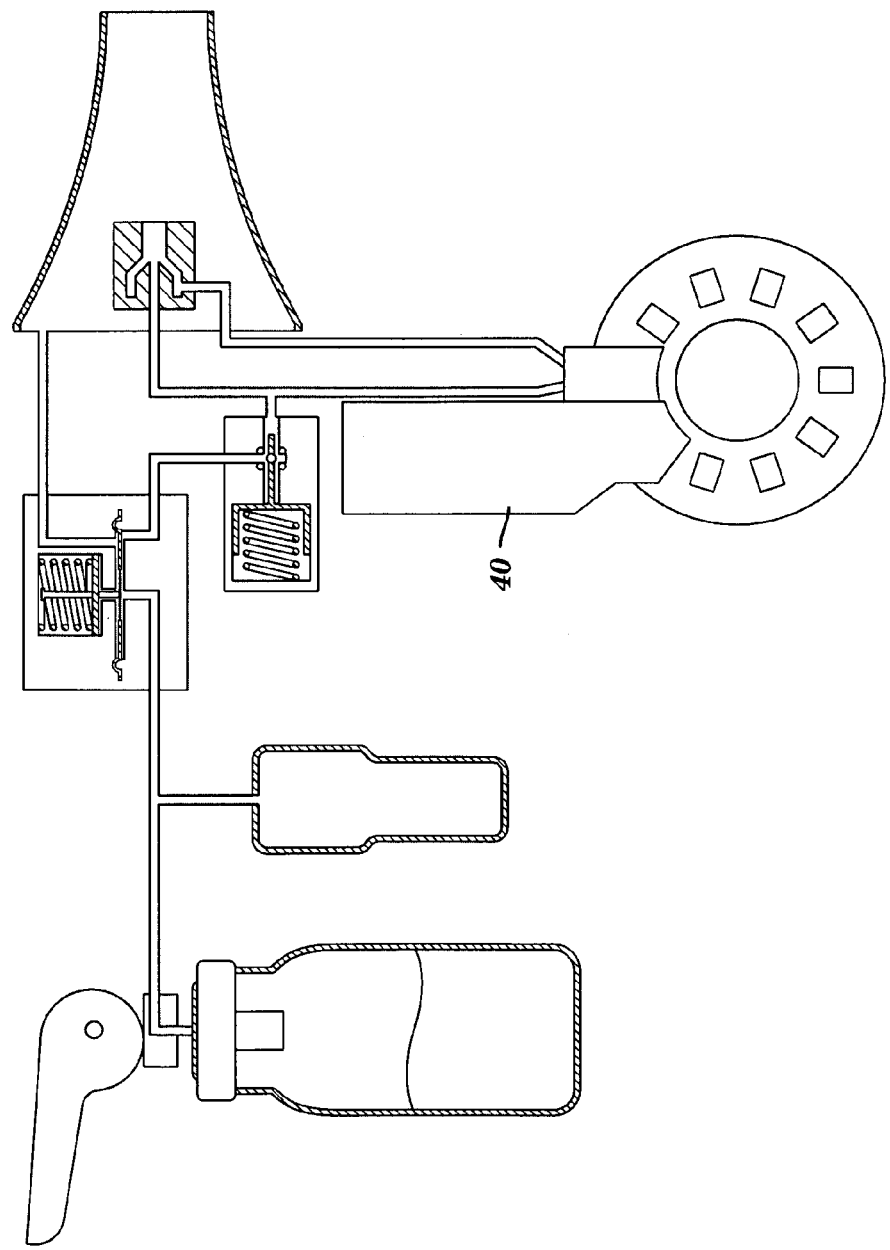
Figure 8B:
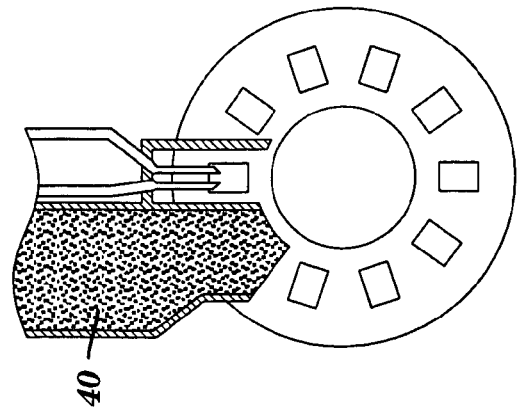
Figure 8C:
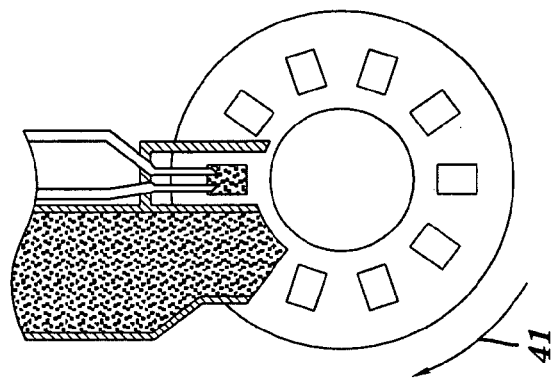
Figure 8D:
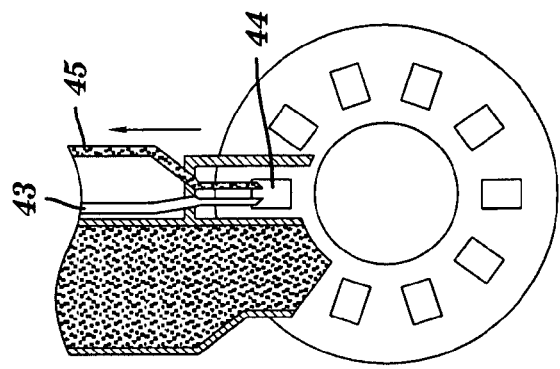

FIGS. 6A-C are an enlarged representation of the assembly illustrated in FIGS. 3A-C.

FIGS. 7A-E is are a schematic representation of a Technohaler system; and

FIGS. 8A-D is are a schematic representation of a Clickhaler system.

Figure 1A:
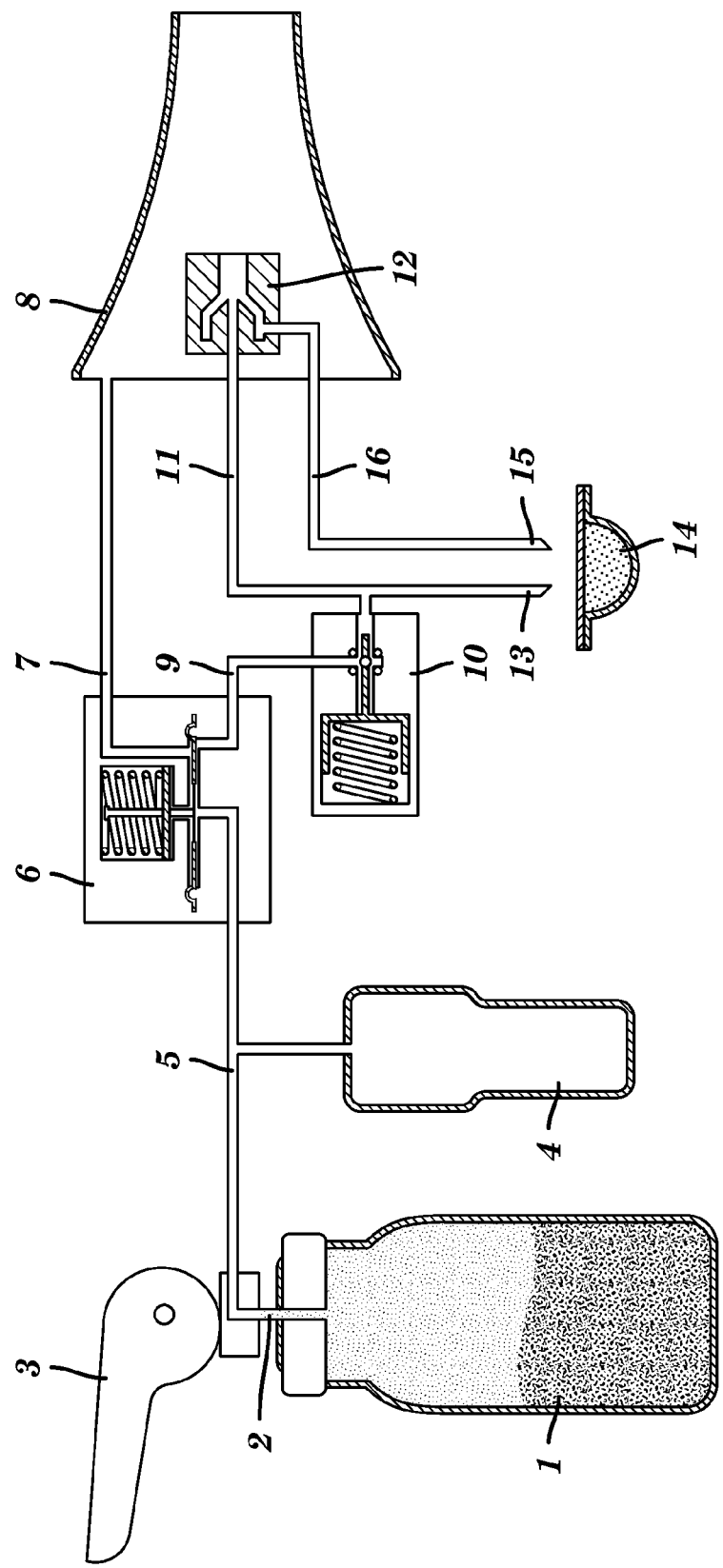
Figure 1B:
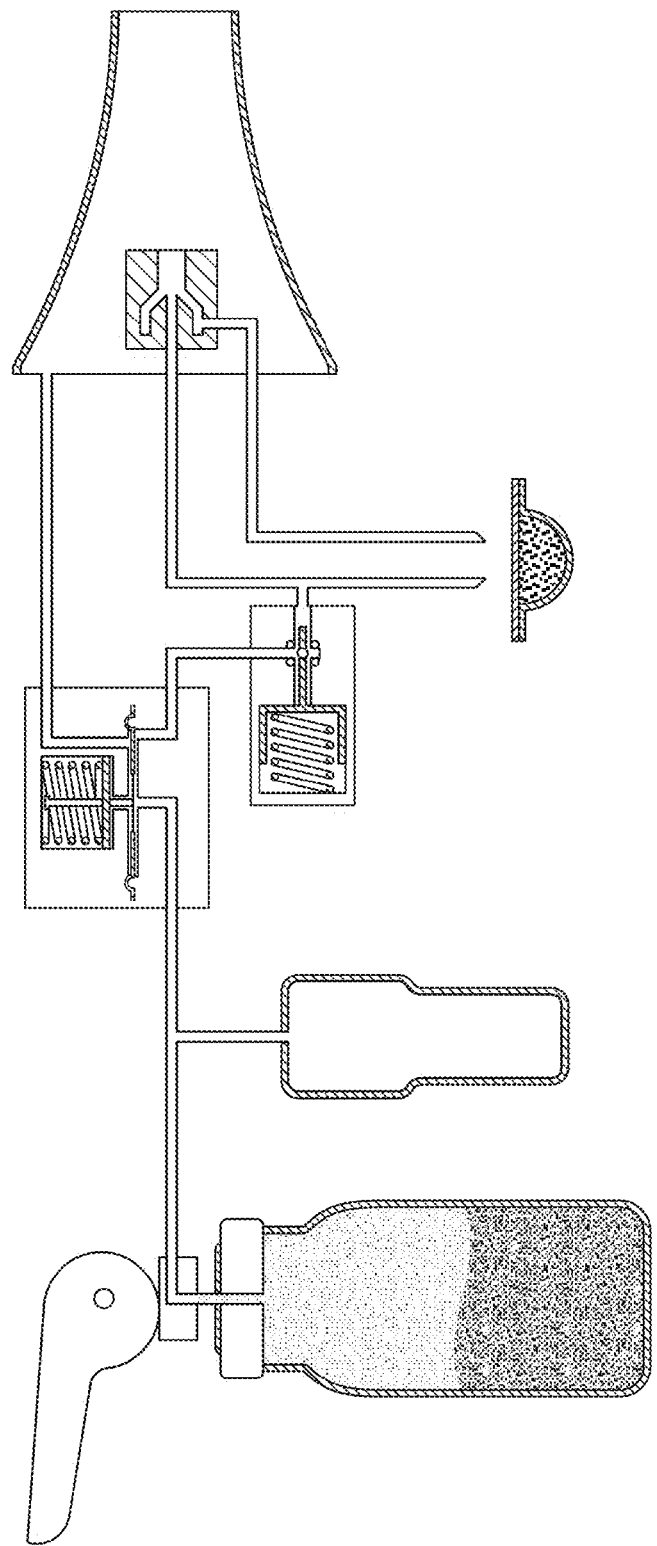
Figure 1C:
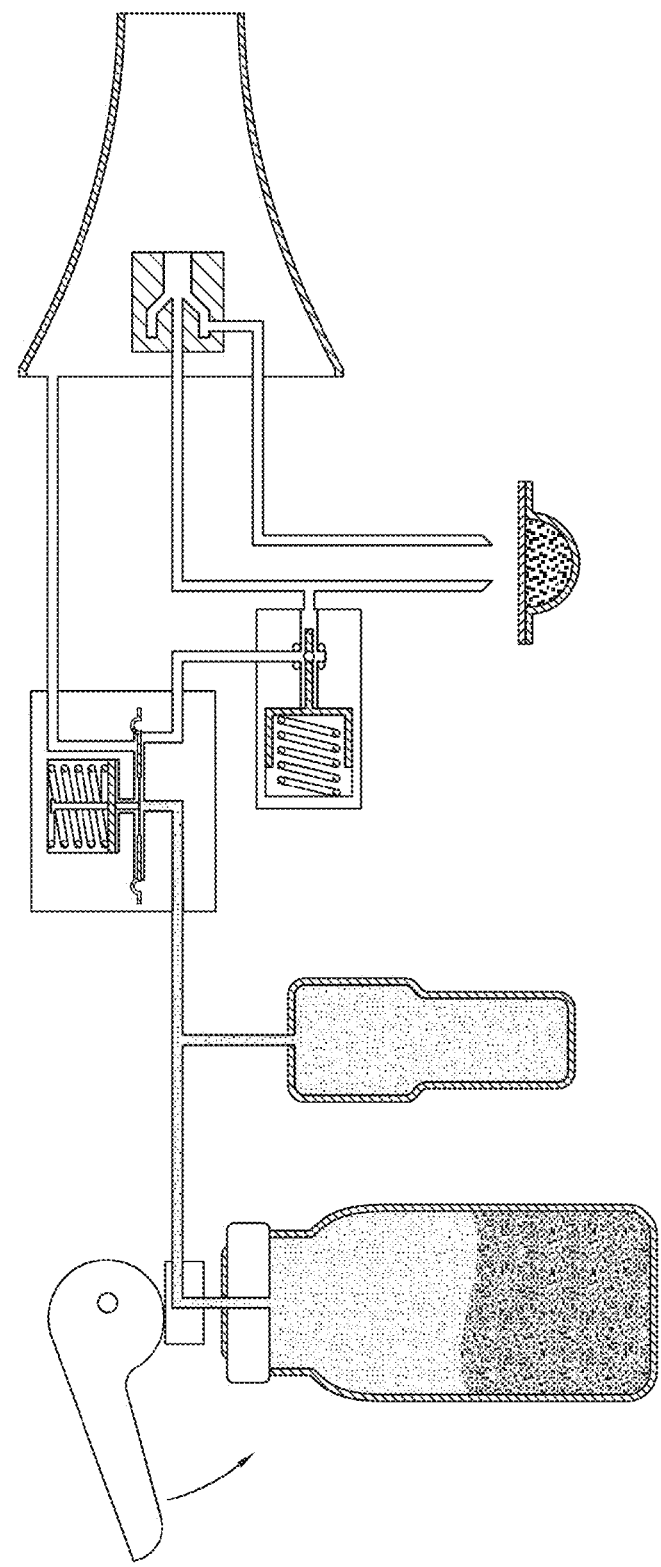
Figure 1D:
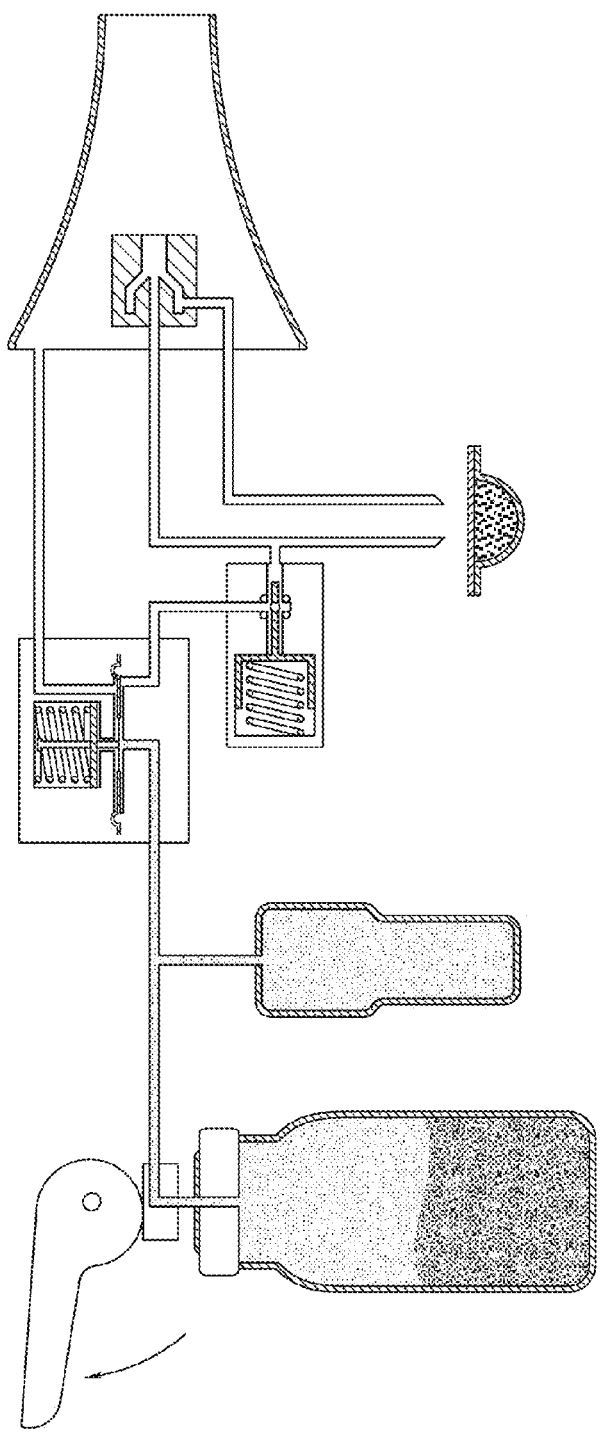
Figure 1E:
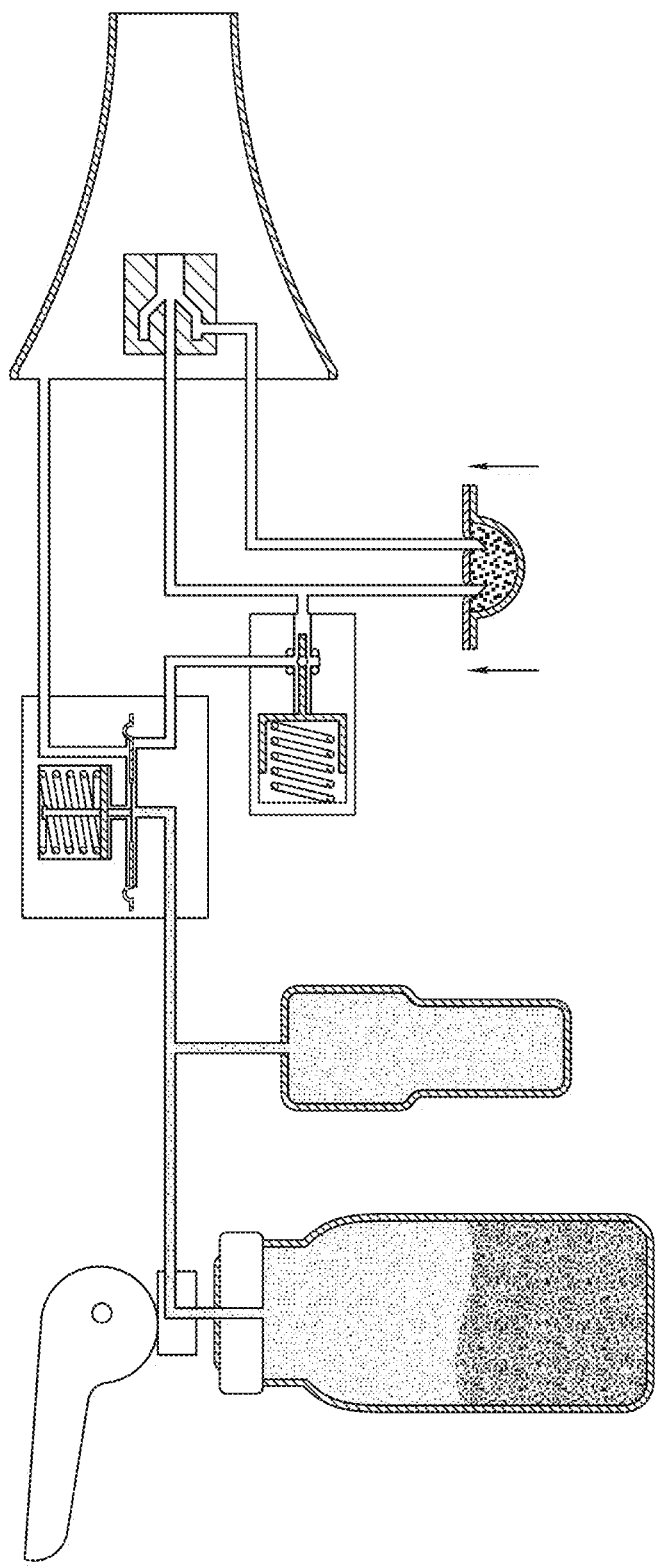
Figure 1F:
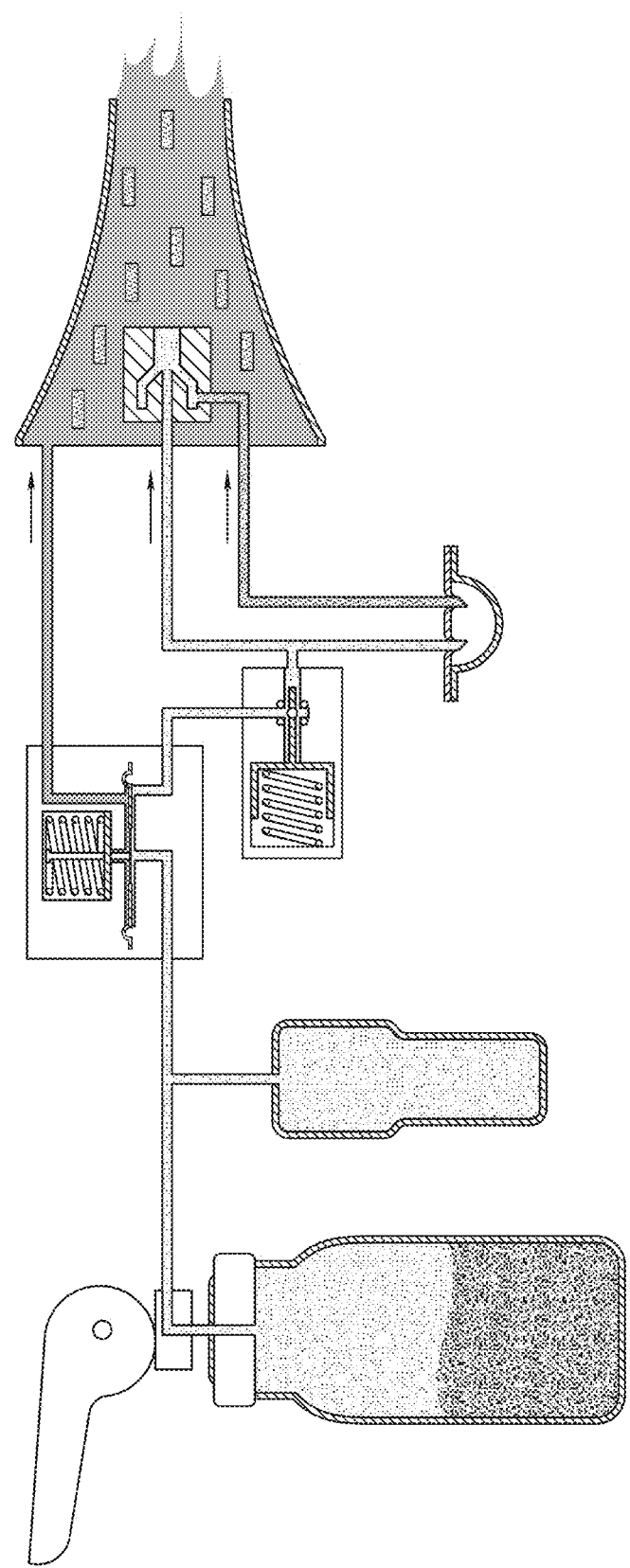

FIG. 1A is a schematic GA showing the principal elements of the devices;

FIGS. 1B to 1F schematically show their operating sequence.

Referring to FIGS. 1A-F schematic illustration of the assembly of the invention shows the assembly with a power source in the form of a canister of propellant (1). In operation, the valve (2) is opened by operation of lever (3) compressed gas fills reservoir (4) via conduit (5) lever (3) is operated to close valve (2) the assembly is now primed. Co-incident with this, the drug container (14) is moved toward orifices (13) and (15) the orifices (13) and (15) which are fashioned in the shape of sharp hollow needles pierce the lid of contained (14) thereby making a sealed connection to the inside of container (14).

Compressed gas is retained in the reservoir (4) and conduit (5) by a diaphragm valve (6). Conduit (7) connects the mouthpiece (8) to the vacuum side of the diaphragm valve (6) the patient (not shown) places the mouthpiece to their mouth and inhales, the diaphragm valve (6) is subjected to a vacuum, when the vacuum reaches the present level, diaphragm valve (6) opens releasing the gas stored in reservoir (4) through conduit (9) to pulsing valve (10). The pulsing valve (1) releases the compressed gas in short rapid pulses through conduit (11) into the air amplifier (12) and outlet orifice (13).

The compressed gas passing through the air amplifier (12) creates a vacuum in conduit (16) drawing medicament and gas mix from the container (14).

The forgoing described the principle of operation of the assembly in its preferred embodiment, however it should be appreciated that there are various approaches to each element of the assembly that achieve the same end, some of which are described in the following text.

Figure 2A:
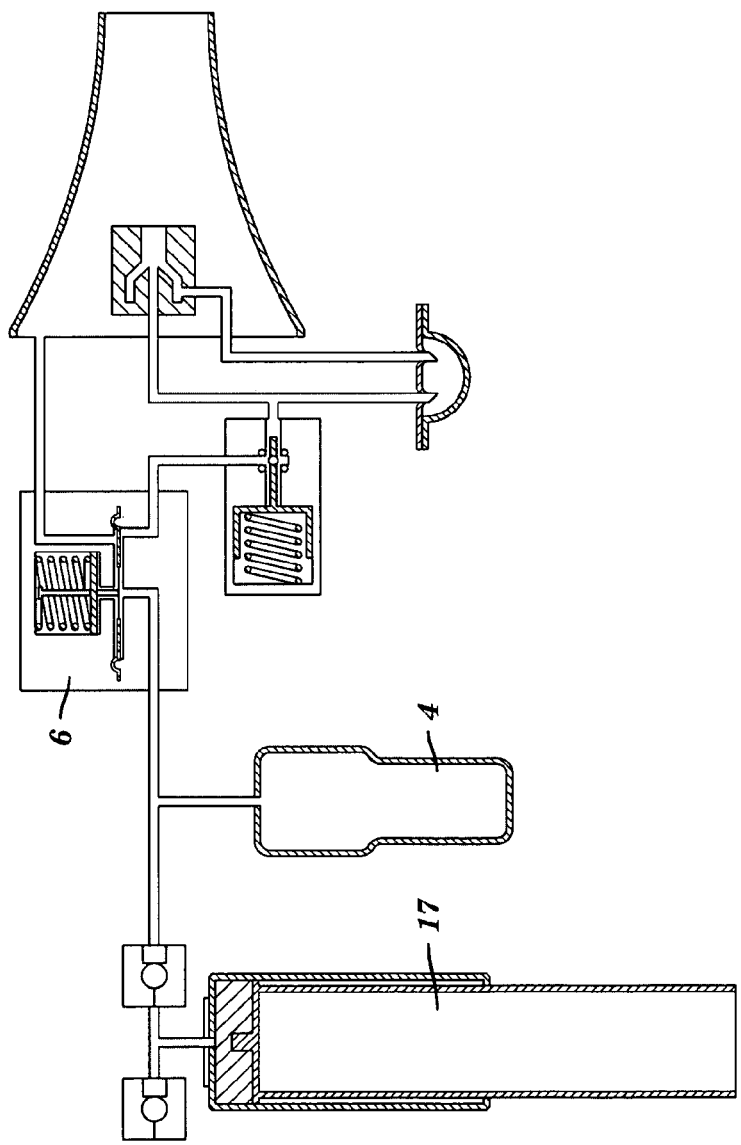
Figure 2B:
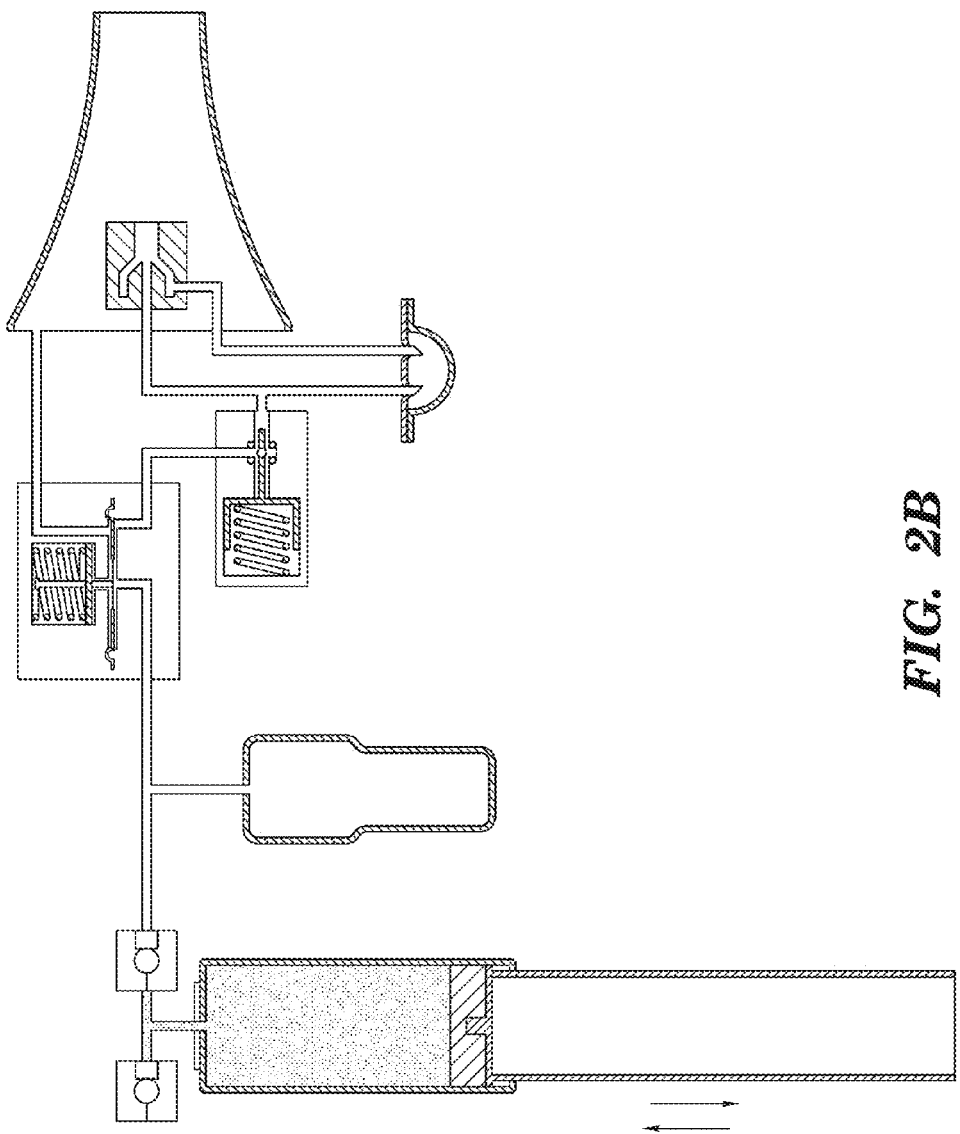
Figure 2C:
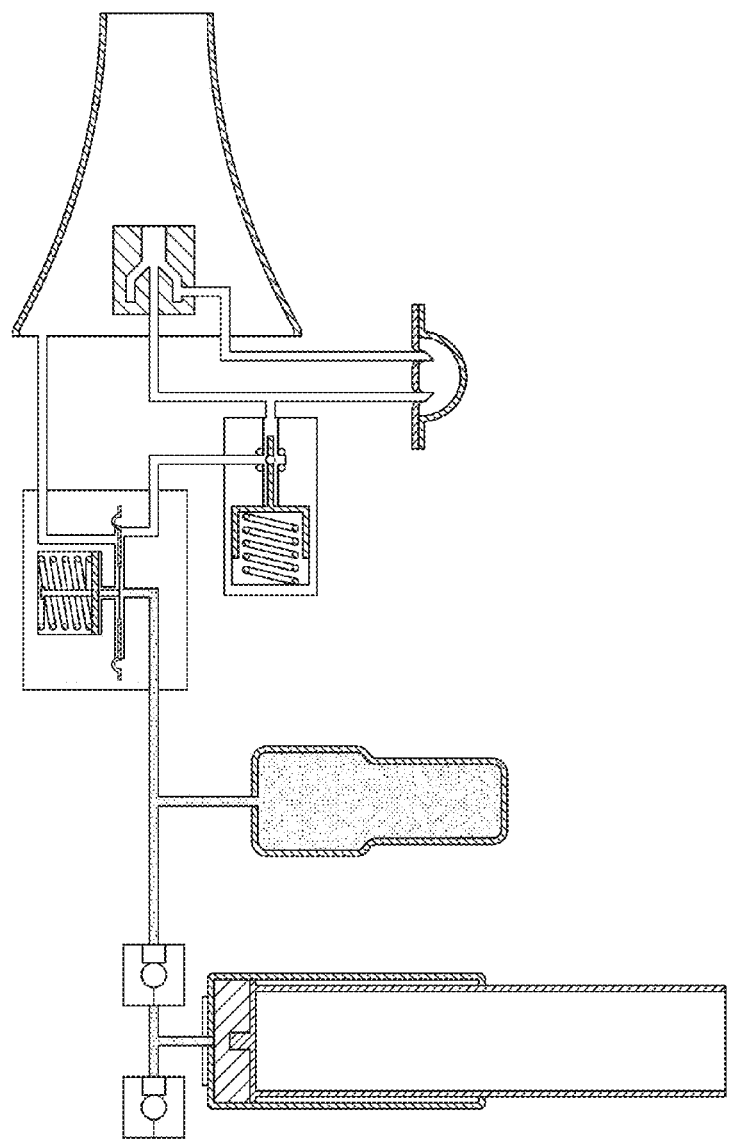

Referring to FIGS. 2A-C, which are schematic diagrams showing the compressed gas source as a manually operated pump (17) in this assembly the patient primes the system by operating the pump lever at least once to charge reservoir (4). It will be appreciated that the source of compressed gas or air can be derived in numerous ways, an electric driven compressor for example and is not limited to those methods described.

The forgoing has described an assembly where the compressed gas is stored in a reservoir (4) a feature of the assembly using this approach is that the length of time the assembly is active from the point diaphragm valve (6) is actuated is determined by the column of compressed gas contained in the reservoir coupled with the flow rate through the assembly. Clearly the pressure of gas available from the reservoir starts to deplete as soon as the assembly is activated, in the preferred embodiment this is adequate, but alternative arrangements can be used for example it may be desirable that the gas pressure in the assembly remains constant throughout the delivery cycle, this can be achieved by providing a reservoir (18) that contains a moving piston (19) See FIGS. 3A-C. In this arrangement the compressed gas enters the reservoir (18) at port (20), showing via a control valve (not shown) the air (or gas) on the opposite side of the piston (19) is driven forward until it reaches the end of the reservoir (18) resulting in a virtually square (pressure time) pulse. A further alternative approach is to use a control valve (21) that produces a square pulse, in this arrangement the compressed gas enters the valve (21) the spool (22) is operated by external force compressed gas enters the assembly and into a reservoir (23) via a orifice (24) when the pressure in the reservoir (23) is sufficient for the piston (25) to drive the spool (2) to its closed position.

Referring back to the above described assembly where the reservoir (18) containing a piston is utilised, a further advantage inherent in this assembly is that the compressed gas energy source can be isolated from the gas (or air) in the assembly that comes into contact with the drag and or patient.

In one embodiment shown in the schematic the container is a shape formed from sheet material (26) or foil with a foil or foil laminate lid (27), this type of container is well known and often described as blister packaging. A single blister may be installed in the assembly for use or a number of blisters may be retained in the assembly with an index mechanism that presents one blister or a combination of blisters to the pick-up position. The pattern or relationship of the blister one to another may take a variety of forms such as but not limited to a circle or disk of blisters or strip of blisters either of limited straight lengths or coiled in the form of a tape.

Blisters may be arranged in a square, rectangle or other geometric shape and each blister presented to the pick-up position by movement of the pack by X and Y movement. The proposed assembly can also pick up/aerosolise from more than one blister on one actuation.

An alternative form of container may be employed such as that described in European Patent No. 0 626 689—(Technohaler), International Patent application No. WO 01/30430 (Cup & Cap) or UK Patent application No. GB 0113881.7 (foil cutting). An example of one alternative arrangement utilising the principle of unit dose delivery described in European Patent No. 0 626 689 is illustrated in FIGS. 7A-E. A spool (30) is loaded with medicament formulation (35) in a spool holder (31), in use the spool (30) is pushed from its first position to a second position at an inlet (34) and of the air amplifier (12). The spool (30) and the medicament (35) are brought into communication with opening (32) in the spool holder (31). The compressed gas orifice (13) is also in communication with an opening (33) in the spool holder on operation of the assembly, powder is drawn from the spool/spool holder via opening (32) whilst compressed gas enters the spool/spool holder assembly via opening (33) air/powder becomes a turbulent mix and is flushed from the contained (spool/spool holder assembly).

A third alternative means of presenting drug formulation to the pick-up position could take the form of metering used in conventional bulk storage dry powder inhalers such as that described in European Patent No. 0 539 469 (Clickhaler).

Referring to FIGS. 8A-D, a drug formulation is stored in a reservoir (4) a metered amount of drug formulation is moved from the reservoir (4) by partial rotation of the cone (41) to a position in line with the intake of air amplifier (42) when compressed gas flows through jet (43) powder is lifted from the cup (44) and expelled through nozzle (45). In the preferred embodiment the powder is replaced by ambient air entering at opening (46). However, a jet of compressed gas may be employed as an alternative to ambient air to aid flushing of powder from in particular, large metering cups.

What is claimed:

1. A medicament delivery assembly comprising a medicament container and a pulse valve, wherein the assembly is adapted to direct a pulsed gas flow, by means of the pulse valve releasing a gas in a plurality of short, rapid pulses, into the medicament container on a single actuation of the assembly.

2. A medicament delivery assembly as claimed in claim 1, wherein the pulse valve has a cycle of between 10 and 100 cycles/second.

3. A medicament delivery assembly as claimed in claim 1, wherein the pulse valve has a cycle of between 25 and 75 cycles/second.

4. A medicament delivery assembly as claimed in claim 1, wherein the pulse valve is connected to a primer source via an actuatable valve, such that when the actuatable valve is opened, the primer source is activated, thereby causing air to flow to the pulse valve.

5. A medicament delivery assembly as claimed in claim 4, wherein the actuatable valve is a diaphragm valve.

6. A medicament delivery assembly as claimed in claim 4, wherein the assembly is adapted such that when the primer source is activated, air also flows to a mouthpiece.

7. A medicament delivery assembly as claimed in claim 1, wherein the medicament delivery assembly comprises a mouthpiece provided with an air amplifier, the air amplifier being provided with a medicament extraction tube for extracting medicament from the medicament container, and the assembly being adapted to direct the pulsed gas flow to both the medicament container and the air amplifier, such that medicament is extracted from the medicament container.

8. A medicament delivery assembly as claimed in claim 7, wherein the medicament extraction tube is linked to the air amplifier such that non-laminar flow of the medicament is created.

9. A medicament delivery assembly as claimed in claim 7, wherein the medicament extraction tube is connected to a medicament chamber which is an annular chamber adapted to provide non-laminar flow of the medicament.

10. A medicament delivery assembly as claimed in claim 1, wherein the medicament is a powder.

11. A medicament delivery assembly as claimed in claim 1, wherein the assembly comprises an inhaler.

12. A medicament delivery assembly as claimed in claim 11, wherein the inhaler is a dry powder inhaler.

13. A medicament delivery assembly as claimed in claim 11, wherein the inhaler is a metered dose inhaler.

14. A method of administering a medicament which comprises the use of a medicament delivery assembly as claimed in claim 1.

15. A method of treatment of a patient with a respiratory disorder, which comprises administering a medicament using a medicament delivery assembly as claimed in claim 1.

16. A method as claimed in claim 15, wherein the method comprises administration of a medicament by inhalation.

17. A method of treatment of a patient with a systemic disorder which comprises the administration of a medicament using a medicament delivery assembly as claimed in claim 1.

18. A method of treating insulin dependent diabetes which comprises administration of an effective amount of insulin using a medicament delivery assembly as claimed in claim 1.

* * * * *